United States Patent [19]
Borzone et al.

[11] Patent Number: 5,203,595
[45] Date of Patent: Apr. 20, 1993

[54] DOVETAIL-TYPE COUPLING DEVICE AND METHOD

[75] Inventors: Rocco R. Borzone, Emerson; Jay Bichet, Aberdeen; Thomas F. McCarthy, Neshanic Station, all of N.J.

[73] Assignee: Pfizer Hospital Products Group, Inc., New York, N.Y.

[21] Appl. No.: 474,421

[22] Filed: Feb. 2, 1990

[51] Int. Cl.$^5$ .............................. F16L 25/00
[52] U.S. Cl. .................... 285/325; 403/331; 464/19; 285/921; 285/331
[58] Field of Search .............. 285/3, 326, 327, 325, 285/332.1, 331, 233, 913, 921; 403/331, 332, 333, 334; 464/18, 19, 106

[56] References Cited

U.S. PATENT DOCUMENTS

| | | | |
|---|---|---|---|
| 210,923 | 12/1878 | Davies | 285/325 |
| 1,557,743 | 6/1923 | Terrill | 403/331 X |
| 2,717,146 | 4/1953 | Zublin | 464/19 |
| 2,985,469 | 9/1957 | Bowman, Jr. | 285/921 X |
| 3,588,149 | 6/1971 | Demler, Sr. | 285/921 X |
| 4,706,659 | 11/1987 | Matthews et al. | 128/92 |
| 4,790,567 | 12/1988 | Kawano et al. | 285/921 X |

FOREIGN PATENT DOCUMENTS 2560804 9/1985 France .
48313 8/1938 Netherlands .

Primary Examiner—Eric K. Nicholson
Attorney, Agent, or Firm—Peter C. Richardson; Lawrence C. Akers; Elizabeth O. Slade

[57] ABSTRACT

A coupling device and method of coupling especially suitable for coupling multiple components of surgical instruments are provided. A wedging portion provides an interference fit between parts so that a secure connection can be made that will not unintentionally dissociate. In a preferred embodiment, bores and counterbores within dovetail portions are provided. Especially preferred is the use of this coupling device to secure a reamer head to a shaft.

13 Claims, 2 Drawing Sheets

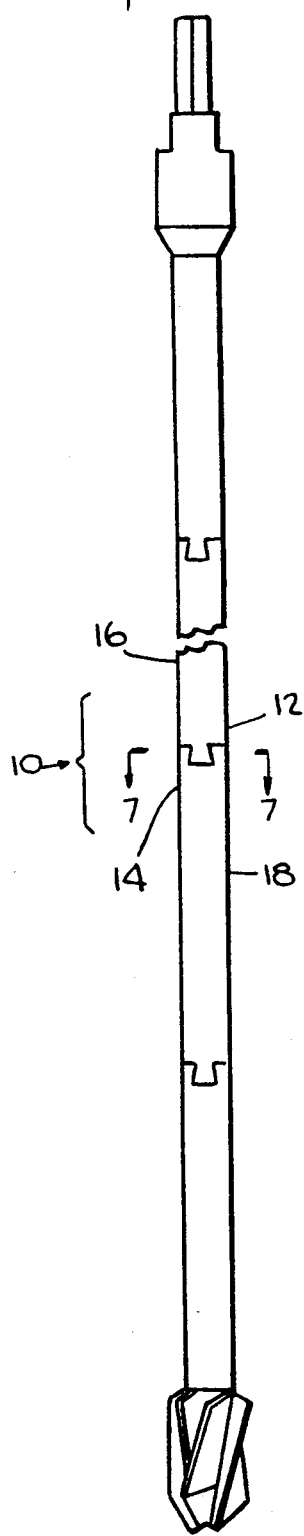
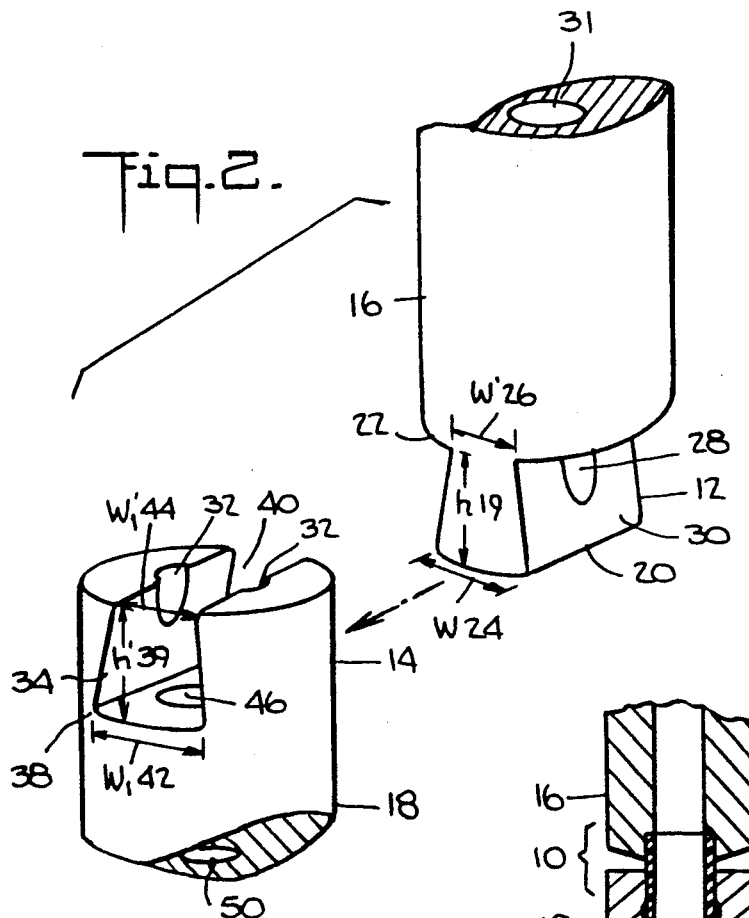
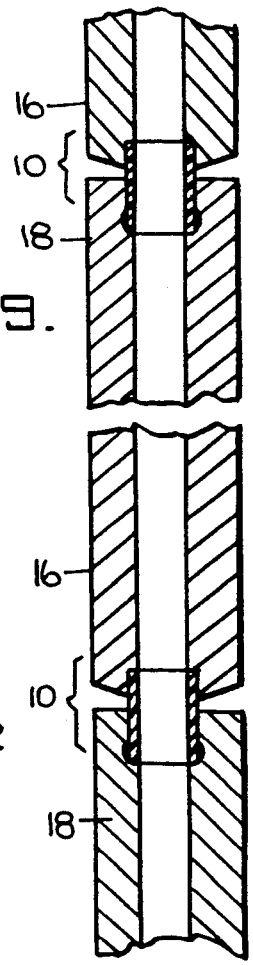
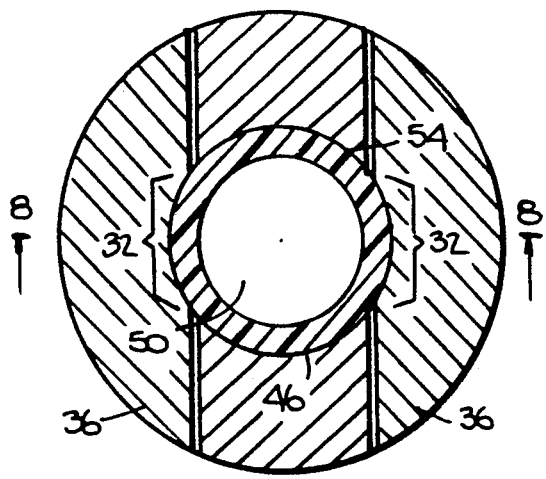

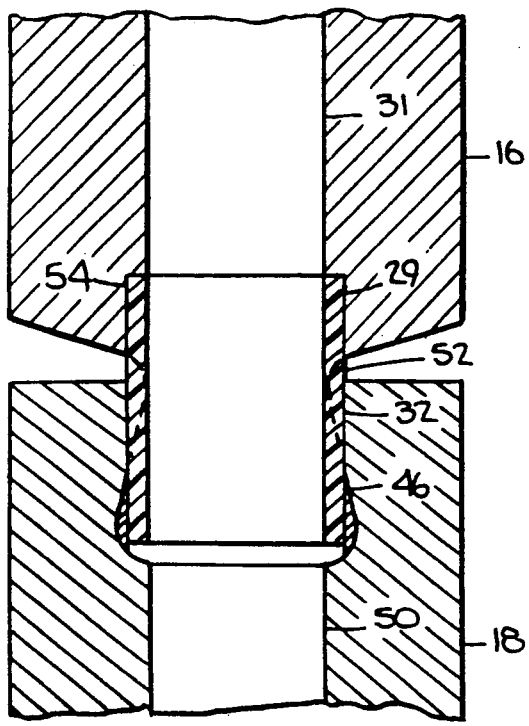
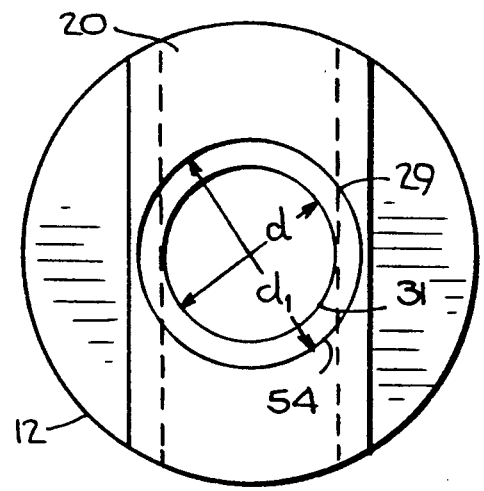
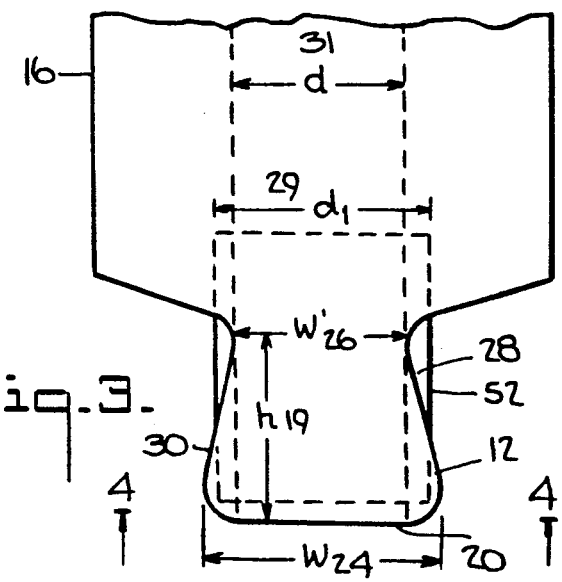
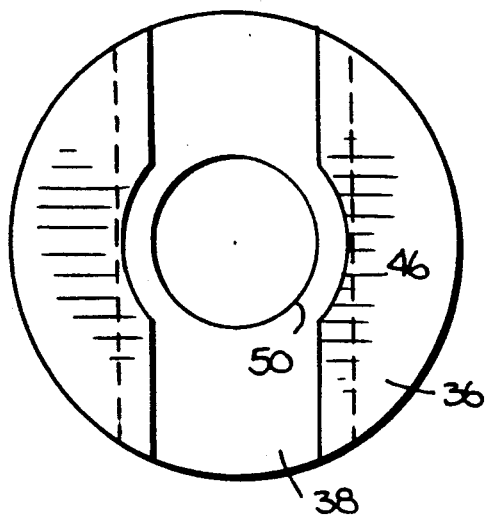
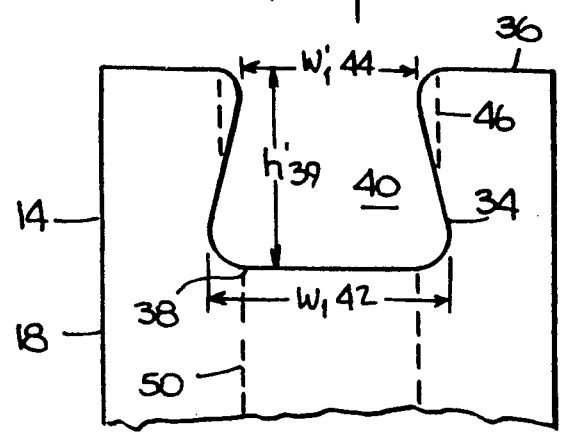

DOVETAIL-TYPE COUPLING DEVICE AND METHOD

BACKGROUND OF THE INVENTION

Multiple component devices are widely used in the area of surgery. The interconnected parts often make use of dovetail connections. The parts sometimes have components which are inserted into the parts so as to keep the parts from separating, for example during surgery.

One example of such a component being used but made of plastic is in U.S. Pat. No. 4,706,659, which describes a flexible connecting shaft.

However, when dovetail connections are used, the tolerances between the mating parts generally should be quite close, especially if a guidewire is not used throughout the procedures. However, production of very close tolerances is costly. Additionally, if the tolerances are not close, the parts will easily dissociate. In an operating room, such dissociation will result in loss of sterile conditions if parts are dropped onto the floor.

An object of the present invention is a device which has parts that can be interlocked securely together and remain together until dissociation is desired.

Another object of the present invention is a surgical device having dovetail connections which can be economically produced and which do not dissociate undesirably, even when a guidewire is not used.

These and other objects are achieved by the apparatus and method of the invention as described below.

SUMMARY OF THE INVENTION

According to the invention, a coupling device comprises two main body parts which are interconnected together with use of a wedging portion made from a flexible material.

In a preferred embodiment, the device comprises a surgical instrument having two mating dovetail parts. The male part of the dovetail has the following characteristics. It has a height h which is the perpendicular distance between the outer end of the male dovetail (which is the widest part of the male dovetail with a width w) and the inner end of the male dovetail (which is the narrowest part of the male dovetail with a width w'). A counterbore is made axially into the wide end of the male dovetail. The diameter d of the counterbore is slightly smaller than w but slightly larger than w', thus resulting in a hole or recess which is located in the side of the dovetail. The depth of the counterbore is preferably slightly greater than h.

Into this counterbore, in a preferred embodiment a flexible material (for example, polypropylene) in the form of a tube is inserted so that the tube preferably bottoms in the counterbore but preferably does not protrude beyond the outer end of the male part of the dovetail; however, the flexible material extends radially out of the hole in the dovetail (described above).

The dovetail has a female portion which has characteristics similar to the male dovetail, but reversed. That is, the width of the innermost end of the recess in this female dovetail portion is slightly larger than w and the width of the outermost end of the recess in this female dovetail portion is slightly larger than w'. This dovetail portion also has a counterbore but with a diameter slightly larger than d. The depth of this counterbore is approximately the height h' of the female dovetail.

Also according to the invention, a method of coupling together a first part and a second part of a multiple component device comprises using a wedging portion made of a flexible material so as to form an interference between the first and second part.

One advantage of the preferred embodiment of the device of this invention is that the tolerances of the male and female portions of the dovetail need not be very close. When the two parts are assembled, the female portion will compress the flexible material until the material enters the counterbore in the female dovetail, where the material will be able to return to its natural shape. Additionally, a slight force will enable the dovetail connection to be disassembled, when desired. The possibility of inadvertent disassembly of the connection is greatly reduced thereby.

Because the tolerances need not be very close, the costs of manufacturing the parts will be reduced. Additionally, the dovetail connection will remain securely assembled until disassembly is desired.

BRIEF DESCRIPTION OF THE DRAWINGS

FIG. 1 is a plan pictorial representation showing a surgical reamer in which three coupling devices of an embodiment of the invention are shown. Full details of all parts of the devices are not shown in FIG. 1 but are described below.

FIG. 2 is a plan pictorial representation showing an embodiment of a dovetail connection into which a tubing of flexible material is to be inserted.

FIG. 3 is a plan view of the male portion of the dovetail shown at the top of FIG. 2, with dotted lines indicating where an insert made of plastic is located therein but protrudes partially therefrom outwardly in a radial direction.

FIG. 4 is a bottom view of FIG. 3 (taken along the line 4—4) showing the bore of diameter d in the male portion of the dovetail and the counterbore of slightly larger diameter $d_1$, in which a plastic insert is shown positioned.

FIG. 5 is a plan view of the female (bottom) portion of the dovetail in FIG. 2, which has a bore and a counterbore located therein into which the plastic insert can protrude when the male and female portions mate together.

FIG. 6 is a top view of the female portion of the device shown in FIG. 5. No plastic is in the female portion here.

FIG. 7 is a cross-sectional view of the device of FIG. 1 taken along the line 7—7 at the smallest width of the male dovetail portion in the direction indicated, showing the plastic insert located substantially within the bore in the male portion but protruding therefrom outwardly in a radial direction into the female portion. This figure is a cross-sectional view of FIGS. 4 and 6 together.

FIG. 8 is a view in cross-section taken along the line 8—8 in FIG. 7 showing the mating male and female portions of the dovetail, together with the wedging portion of flexible material located substantially within the bore of the male portion but protruding in a radial direction out of the male portion of the dovetail and into the counterbore located within the female portion of the dovetail in a preferred embodiment of the invention. Tolerances between the mating dovetail portions are not shown to be close.

FIG. 9 is a view in cross-section showing multiples of the embodiment of the device of the invention that was shown in FIG. 8.

DETAILED DESCRIPTION OF THE DRAWINGS

In FIG. 1, an embodiment of the coupling device of the invention referred to generally as 10 is used in a reamer having multiple segments joined together by dovetail connections, especially a removable cutting head connected to a shaft by such a coupling device. A preferred coupling device of the invention comprises a male dovetail portion, the mating female dovetail portion, and a wedging portion made of a flexible material (not shown in detail in FIG. 1 but described hereinafter).

In FIG. 2, dovetail male portion 12 is shown separated from dovetail female portion 14. Dovetail male portion 12 is an integral part of first part 16 of the multiple component device which (in this embodiment) is in the form of a cylinder; and dovetail female portion 14 is an integral part of second part 18 of the multiple component device which (in this embodiment) is also in the form of a cylinder.

Dovetail male portion 12 has a height h 19, which is the perpendicular distance between the outer end 20 and inner end 22 of dovetail male portion 12. The width of the dovetail at end 20 (which is the widest part of the male part of the dovetail) is w 24. The width of the male part of the dovetail at end 22 (which is the narrowest part of the dovetail) is w' 26.

Also shown in FIG. 2, located within dovetail male portion 12 is a hole or recess 28 which when viewed in a direction perpendicular thereto appears to be substantially triangular-shaped, with curved corners on the triangle. This recess 28 is formed on each side 30 of male dovetail portion 12 at the intersection of each side 30 with the counterbore 29 (not shown in FIG. 2) located within dovetail male portion 12. First bore 31 in first part 16 has a diameter somewhat smaller than counterbore 29.

Also in FIG. 2 in dovetail female portion 14 are shown recesses 32. Each of these recesses 32 also appears to be substantially triangular-shaped when viewed in a direction substantially perpendicular to the surface of side 34 of dovetail female portion 14. As can be seen in FIG. 2, the upper boundary of each of recesses 32 is an arc of a circle. Dovetail female portion 14 has an inner end 38. The perpendicular distance h' 39 between outer end 36 of dovetail female portion 14 and inner end 38 of dovetail female portion 14 is preferably slightly larger than h 19, described above. Additionally, recess 40 (which is the space within dovetail female portion 14 into which dovetail male portion 12 fits) has a largest width $w_1$ 42 (at or near end 38) which is slightly larger than width w 24 described above. Recess 40 at outer end 36 of dovetail female portion 14 has a width $w_1'$ 44, which is slightly larger than w' 26 described above. Recess 32 is a portion of the counterbore 46 located within female dovetail portion 14 and counterbore 46 has a diameter somewhat larger than the bore 50 in second part 18.

First bore 31 and second bore 50 will be further described below.

In FIG. 3, dovetail male portion 12 (which is an integral part of first part 16) is shown, with first bore 31 and counterbore 29 shown in dotted lines. Also shown is a portion 52 of flexible material which protrudes outwardly in a radial direction through recess 28. Portion 52 of flexible material is a portion of flexible tubing 54, the major portion of which is located within counterbore 29, the tubing having an inner diameter which is approximately equal to the diameter d, of first bore 31.

In FIG. 4, which shows the bottom of male portion 12 of the dovetail, the flexible tubing 54 is located within counterbore 29 in male portion 12 of the dovetail. First bore 31 in male portion 12 is shown.

In FIG. 5, female portion 14 of the dovetail is shown with second bore 50 and second counterbore 46 located therein. Inner end 38 and outer end 36 are also shown, together with h'39, $w_1$ 42, $w'_1$ 44, and recess 40.

In FIG. 6, second bore 50 and second counterbore 46 in female portion 14 are shown, as well as end 36 of female portion 14. End 38 is also shown. Bore 50 and counterbore 46 are located at different levels within second part 18, as shown clearly in FIG. 5.

In FIG. 7, flexible tubing 54 is shown. Bore 50 is also shown, together with counterbore 46. Flexible tubing 54 protrudes out of recesses 28 (shown in FIG. 2) and protrudes into recess 32 within female portion 18 (shown in FIG. 2.)

In FIG. 8, the dovetail male portion 12 and dovetail female portion 14 are shown in a mating position. First bore 31 in male portion 12 is shown aligned substantially coaxially with second bore 50 in female portion 14. Counterbore 29 in male portion 12 is shown, as is counterbore 46 in female portion 14. A portion 52 of flexible material is shown extending out of first bore 31 in male portion 12 and into recess 32 in female portion 14. Flexible tubing 54 is also shown. Portion 52 of flexible tubing 54 forms a wedging portion between male portion 12 and female portion 14.

The male dovetail portion 12, female dovetail portion 14, and wedging portion 52 taken together form a preferred embodiment of the coupling device of the invention.

In FIG. 9, are shown two of the preferred embodiment of the device of the invention which was shown in FIG. 8. If desired, no guidewire need be used with the coupling devices of the invention.

The use of the flexible material in the form of tubing and the use of the counterbores in the male and female portions keep the two mating parts centrally located and allow the flexible material to return to its natural shape so that a guidewire, if used, can pass through the bore of the device.

The flexible material to be used in the device and method of the invention can be any suitable flexible material. Especially preferred is material which can be molded into the shape of tubing, for example, polypropylene or any other suitable material.

The coupling device can be made by the following procedure. Any multiple-component device for use as a single device can be made with any suitable connection, for example a dovetail connection. If bores are located within the multiple components, a counterbore of a diameter slightly larger than the diameter of the bore will preferably be made in the male portion of the dovetail and another counterbore will be made in the female portion of the dovetail. The male portion counterbore should have a diameter which is slightly smaller than the largest width of the male dovetail portion and should also have a diameter which is slightly larger than the smallest width of the male dovetail portion, so as to provide a recess in the side of the male dovetail connection through which some of the flexible material can protrude. This protruding flexible material forms an interference between the mating parts of the dovetail.

We claim:

1. A coupling device comprising:
   (a) a first part having a protrusion extending therefrom, said protrusion being in the form of a dovetail and having a planar first surface and a pair of wall surfaces extending from said planar first surface at an angle with respect to said planar first surface;
   (b) a second part having a recess into which said protrusion can mate, said recess being in the form of a dovetail recess having a planar second surface and a pair of wall surfaces extending from said planar second surface at an angle with respect to said planar second surface; and
   (c) a wedging portion formed from flexible material and situated in a fixed position between at least one wall surface of said recess and said protrusion such that said wedging portion provides an interference between said first part and said second part when said first part and said second part mate together as said protrusion fits within said recess, thus preventing said first part from readily separating from said second part and thus tightening said first part with respect to said second part so that extremely close tolerances between said protrusion and said recess are not necessary,
   wherein said protrusion of said first part is a male dovetail portion and said recess in said second part is a female dovetail portion and wherein said wedging portion is formed from flexible plastic material.

2. A device according to claim 1, wherein said first part has a first bore located therein, wherein said second part has a second bore located therein, and wherein said first bore and said second bore are positioned substantially coaxially with respect to each other when said first part and said second part mate together.

3. A device according to claim 2, wherein said wedging portion is in the form of a cylinder and is located substantially within said first bore in said first part.

4. A device according to claim 3, wherein the major extent of said first part and the major extent of said second part are both substantially cylindrically shaped.

5. A device according to claim 4, wherein said wedging portion comprises a cylinder of plastic material which protrudes at least to some extent in a radial direction out of the male portion of said dovetail and wherein said female portion of said dovetail has a second counterbore located therein into which a portion of said wedging portion can fit.

6. A device according to claim 5, wherein said male portion of said dovetail has a height h which is the perpendicular distance between (a) the outer end of said male portion of said dovetail (which has a largest width w) and (b) the inner end of said male portion of said dovetail (which has a smallest width w'),
   and wherein said male portion of said dovetail has a first counterbore located therein which has a diameter slightly smaller than w but slightly larger than w'.

7. A device according to claim 6, wherein the height h of said male portion of said dovetail is slightly smaller than the depth of said first counterbore.

8. A device according to claim 7, wherein said cylinder of plastic material is a hollow cylinder and wherein when said male portion and said female portion are in a mating position, said first bore and said second bore are substantially coaxial and wherein said first part is made of metal, wherein said second part is made of metal, and wherein said female dovetail portion is integral with a reamer head.

9. A method of coupling together a first part and a second part of a multiple component device, wherein said first part has a protrusion extending therefrom and wherein said second part has a recess into which said protrusion can mate,
   said protrusion being in the form of a dovetail and having a planar first surface and a pair of wall surfaces extending from said planar first surface at an angle with respect to said planar first surface and
   said recess being in the form of a dovetail recess having a planar second surface and a pair of wall surfaces extending from said planar second surface at an angle with respect to said planar second surface;
   said method comprising inserting a wedging portion made of a flexible material in a fixed position internally and laterally between at least one wall of said recess and said protrusion such that said wedging portion provides an interference between said first part and said second part when said first part and said second part mate together as said protrusion fits within said recess, thus preventing said first part from readily separating from said second part and thus tightening said first part with respect to said second part so that extremely close tolerances between said protrusion and said recess are not needed,
   wherein said first part has as an integral part thereof a male dovetail portion, wherein said second part has as an integral part thereof a female dovetail portion, wherein said wedging portion comprises a cylinder of flexible plastic material, wherein said male dovetail portion has a first bore and a first counterbore located therein and wherein said female portion of said dovetail has a second bore and a second counterbore located therein, and wherein said first bore and said second bore are positioned substantially coaxially with respect to each other when said first part and said second part mate together, wherein said wedging portion in the form of a cylinder is located substantially within said first bore in said first part, and wherein said cylinder protrudes at least to some extent in a radial direction out of said male dovetail portion and into said second counterbore.

10. A method according to claim 9, wherein said male portion of said dovetail has a height h which is the perpendicular distance between the largest width w of said male dovetail and the smallest width w' of said male dovetail, and wherein said first counterbore has a diameter which is slightly smaller than w and slightly larger than w'.

11. A device according to claim 3, wherein said wedging portion comprises a cylinder of plastic material which protrudes at least to some extent in a radial direction out of the male portion of said dovetail and wherein said female portion of said dovetail has a counterbore located therein into which a portion of said wedging portion can fit.

12. A coupling device comprising:
   (a) a first part having a protrusion extending therefrom, wherein said protrusion is in the form of a dovetail and has a planar first surface and a pair of wall surfaces extending from said planar first surface at an angle with respect to said planar first surface;

(b) a second part having a recess into which recess said protrusion can mate, wherein said recess is in the form of a dovetail recess having a planar second surface and a pair of wall surfaces extending from said planar second surface at an angle with respect to said planar second surface; and (c) a wedging portion formed from flexible material and situated in a fixed position within said recess such that said wedging portion extends laterally beyond a portion of a wall surface of said protrusion and said recess such that said wedging portion provides an interference between said first part and said second part when said first part and said second part mate together, thus preventing said first part from readily separating from said second part in a lateral direction and thus tightening said first part with respect to said second part in a lateral direction until dissociation is desired.

13. A method of coupling together a first part and a second part of a multiple component device, wherein said first part has a protrusion extending therefrom, wherein said protrusion is in the form of a dovetail and has a planar first surface and a pair of wall surfaces extending from said planar first surface at an angle with respect to said planar first surface, wherein said second part has a recess into which said protrusion can mate, wherein said recess is in the form of a dovetail recess having a planar second surface and a pair of wall surfaces extending from said planar second surface at an angle with respect to said planar second surface, said method comprising:

(a) inserting a wedging portion made of a flexible material in a fixed position internally within said recess such that said wedging portion extends laterally beyond a portion of the surface of at least one wall surface such that said wedging portion provides an interference between said first part and said second part when said first part and said second part mate together, thus preventing said first part from readily separating in a lateral direction from said second part and thus tightening said first part with respect to said second part in a lateral direction until dissociation is desired.

* * * * *